United States Patent [19]

Picard et al.

[11] Patent Number: 5,364,882
[45] Date of Patent: Nov. 15, 1994

[54] OXYSULFONYL UREA ACAT INHIBITORS

[75] Inventors: Joseph A. Picard; Drago R. Sliskovic, both of Ypsilanti, Mich.

[73] Assignee: Warner-Lambert Company, Morris Plains, N.J.

[21] Appl. No.: 984,028

[22] Filed: Dec. 1, 1992

Related U.S. Application Data

[60] Division of Ser. No. 736,678, Jul. 26, 1991, Pat. No. 5,198,466, which is a continuation-in-part of Ser. No. 611,245, Nov. 9, 1990, abandoned.

[51] Int. Cl.$^5$ .................. A61K 31/255; C07C 309/63
[52] U.S. Cl. ........................ 514/517; 558/50
[58] Field of Search ................ 558/50; 504/214, 329; 514/517

[56] References Cited

U.S. PATENT DOCUMENTS

| | | | |
|---|---|---|---|
| 4,191,553 | 3/1980 | Reap | 504/214 X |
| 4,394,153 | 7/1983 | Reap | 504/214 |
| 4,581,059 | 4/1986 | Adams et al. | 504/214 |
| 4,678,500 | 7/1987 | Hay et al. | 504/214 |
| 5,102,443 | 4/1992 | Kehne et al. | 504/214 |
| 5,110,975 | 5/1992 | Schroeder et al. | 558/44 |
| 5,198,466 | 3/1993 | Picard et al. | 558/50 X |
| 5,220,041 | 6/1993 | Buckland | 549/493 |

OTHER PUBLICATIONS

Kehne et al, Chemical Abstracts, vol. 112, #216967z (1990).
Bartmann, Chem. Ber., vol. 100, pp. 2938 to 2945 (1967).
Montero et al, Tetrahedron Letters, vol. 24 (30), pp. 3091 to 3094 (1983).
Lattrell et al, Chem. Ber., vol. 105, pp. 2800 to 2804 (1972).

*Primary Examiner*—Floyd D. Higel
*Attorney, Agent, or Firm*—Michael J. Atkins; Charles W. Ashbrook

[57] ABSTRACT

Compounds of the formula

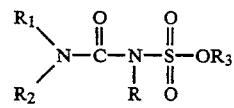

wherein R is hydrogen, a straight or branched alkyl group having from 1 to 8 carbon atoms or benzyl; wherein each of $R_1$ and $R_2$ is hydrogen, an aralkyl group, a straight or branched hydrocarbon group having from 1 to 20 carbon atoms and may be saturated or unsaturated, an alkyl group of from 1 to 6 carbon atoms wherein the terminal carbon is substituted, the group —$(CH_2)_p$—Q wherein p is zero to three and Q is a 5- or 6-membered monocyclic or fused bicyclic heterocycle, phenyl or $NR_1R_2$ taken together form a monocyclic heterocyclic ring, and $R_3$ is phenyl, substituted phenyl, naphthyl, substituted naphthyl, —$(CH_2)_p$—Q wherein p and Q are as defined above, an aralkyl group or a straight or branched hydrocarbon group having from 1 to 20 carbon atoms and being straight or branched, which compounds are useful in treating hypercholesterolemia.

11 Claims, No Drawings

OXYSULFONYL UREA ACAT INHIBITORS

CROSS-REFERENCE TO RELATED APPLICATION

This is a division of Ser. No. 736,678 filed Jul. 26, 1991, now U.S. Pat. No. 5,198,466, which is a continuation in part of Ser. No. 611,245 filed Nov. 9, 1990, now abandoned.

BACKGROUND OF THE INVENTION

This invention relates to chemical compounds having pharmacological activity, to pharmaceutical compositions which include these compounds, and to a pharmaceutical method of treatment. More particularly, this invention concerns certain novel compounds which inhibit the enzyme acylcoenzyme A: cholesterol acyltransferase (ACAT), pharmaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which could be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

INFORMATION DISCLOSURE STATEMENT

Chem. Ber. 100(9), 2938–2945 (1967) describes the following compounds wherein Ph is phenyl. No use is described for the compounds.

$$R_1HN-\underset{O}{\underset{\|}{C}}-NH-\underset{O}{\overset{O}{\underset{\|}{\overset{\|}{S}}}}-OR^2$$

| $R^1$ | $R^2$ |
|---|---|
| Ph | 4-ClPH |
| Ph | 2,6-diCH$_3$Ph |
| Ph | 2-Clpropyl |
| n-butyl | —CH=CH$_2$ |
| C$_6$H$_{11}$ | 2,6-diCH$_3$Ph |
| Ph | —CH=CH$_2$ |

Chem. Ber. 105, 1972, 2800–2804 describes the following compounds for which no use is described.

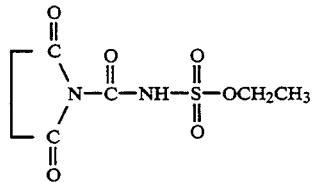

Tetrahedron Letters 24(30), 3091–3094 describes the following compounds wherein Ph is phenyl. No utility is set forth for these compounds.

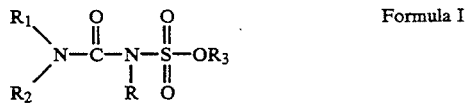

| R |
|---|
| Ph |
| 4-ClPh |
| 4-biphenylyl |
| α-CH$_3$benzyl |
| CH$_3$(CH$_2$)$_4$— |

SUMMARY OF THE INVENTION

The present invention provides a class of compounds which have acyl-CoA: cholesterol acyltransferase (ACAT) inhibitory activity having the following structure:

Formula I $$\underset{R_2}{\overset{R_1}{\diagdown}}N-\underset{R}{\underset{|}{\overset{O}{\underset{\|}{C}}}}-N-\underset{O}{\overset{O}{\underset{\|}{\overset{\|}{S}}}}-OR_3$$

wherein R is hydrogen, a straight or branched alkyl having from 1 to 8 carbon atoms or benzyl;
wherein each of R$_1$ and R$_2$ is selected from
(a) hydrogen,
(b) the group

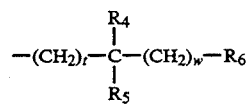

wherein t is zero to 4; w is zero to 4 with the proviso that the sum of t and w is not greater than 5; R$_4$ and R$_5$ are independently selected from hydrogen or alkyl having from 1 to 6 carbon atoms, or when R$_4$ is hydrogen, $R_5$ can be selected from the groups defined for $R_6$; and $R_6$ is phenyl or phenyl substituted with from 1 to 3 substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —$(CH_2)_qNR_7R_8$ wherein $R_7$ and $R_8$ are independently hydrogen or alkyl of from 1 to 4 carbon atoms, and q is zero or one;

(c) a straight or branched hydrocarbon chain having from 1 to 20 carbon atoms and which is saturated or contains from 1 to 3 double bonds;

(d) an alkyl group having from 1 to 6 carbon atoms wherein the terminal carbon is substituted with hydroxy, —$NR_7R_8$ wherein $R_7$ and $R_8$ have the meanings defined above, or —COOalkyl wherein alkyl is straight or branched and has from 1 to 4 carbon atoms;

(e) —$(CH_2)_pQ$ wherein p is a number from zero to 3 and Q is a 5- or 6-membered monocyclic or fused bicyclic heterocycle containing at least 1 to 4 nitrogen, oxygen, or sulfur atoms in at least one ring member;

(f) phenyl or phenyl substituted with from 1 to 3 substituents selected from straight or branched alkyl having from 1 to 6 carbon atoms, alkoxy which is straight or branched and has from 1 to 6 carbon atoms, alkylthio which is straight or branched and has from 1 to 6 carbon atoms, —$(CH_2)_qNR_7R_8$ wherein $R_7$ and $R_8$ and q have the meanings defined above, hydroxy, nitro, chlorine, fluorine, bromine, or trifluoromethyl; or (g) $NR_1R_2$ taken together or form a monocyclic heterocyclic group selected from pyrrolidino, piperidino, morpholino, or piperazino, each of which is unsubstituted or is substituted with one substituent selected from benzhydryl, straight or branched alkyl having from 1 to 6 carbon atoms, phenyl, benzyl, or substituted phenyl or substituted benzyl wherein the substituents vary from 1 to 3 and can be on any position of 2 through 6 of the aromatic ring and are selected from straight or branched alkyl having from 1 to 4 carbon atoms, straight or branched alkoxy having from 1 to 4 carbon atoms, hydroxy, fluorine, chlorine, bromine, trifluoromethyl, or nitro;

wherein $R_3$ is selected from (a) phenyl which is unsubstituted or is substituted with from 1 to 3 substituents selected from:
phenyl,
an alkyl group having from 1 to 6 carbon atoms and which is straight or branched,
an alkoxy group having from 1 to 6 carbon atoms and which is straight or branched,
phenoxy,
hydroxy,
fluorine,
chlorine,
bromine,
nitro,
trifluoromethyl,
—COOH,
—COOalkyl wherein alkyl has from 1 to 4 carbon atoms and is straight or branched,
—$(CH_2)_sNR_9R_{10}$ wherein s is zero or one, and each of $R_9$ and $R_{10}$ is selected from hydrogen or a straight or branched alkyl group having 1 to 4 carbon atoms;

(b) 1- or 2-naphthyl which is unsubstituted or substituted with from 1 to 3 substituents selected from phenyl,
an alkyl group having from 1 to 6 carbon atoms and which is straight or branched;
an alkoxy group having from 1 to 6 carbon atoms and which is straight or branched,
hydroxy,
phenoxy,
fluorine,
chlorine,
bromine,
nitro,
trifluoromethyl,
—COOH, —COOalkyl wherein alkyl has from 1 to 4 carbon atoms and is straight or branched,
—$(CH_2)_sNR_9R_{10}$ wherein s, $R_9$ and $R_{10}$ have the meanings defined above;

(c) the group

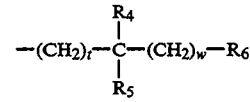

wherein t, w, $R_4$, $R_5$, and $R_6$ have the meanings defined hereinabove;

(d) —$(CH_2)_p$—Q wherein p and Q have the meanings defined hereinabove;

(e) a straight or branched hydrocarbon chain having from 1 to 20 carbon atoms and which is saturated or contains from 1 to 3 double bonds; and pharmaceutically acceptable salts thereof with the provisos that:

(i) both $R_1$ and $R_2$ are not hydrogen at the same time;

(ii) when each of $R_1$ and $R_2$ is the group

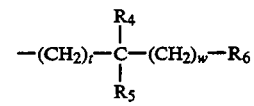

$R_5$ is hydrogen or alkyl having from 1 to 6 carbon atoms; and (iii) the following compounds are excluded:

| $R_1$ | $R_2$ | $R_3$ |
| --- | --- | --- |
| Ph | H | 4-ClPh |
| Ph | H | 2,6-diCH$_3$Ph |
| Ph | H | —CH=CH$_2$ |
| n-C$_4$H$_9$ | H | —CH=CH$_2$ |

This invention also provides pharmaceutical compositions containing the compounds of Formula I and methods of treating hypercholesterolemia and atherosclerosis using the compounds of Formula I as well as the compounds excluded by proviso (iii) above.

DETAILED DESCRIPTION OF INVENTION

The compounds of the present invention provide a novel class of oxysulfonyl ureas which are ACAT inhibitors rendering them useful in treating hypercholesterolemia and atherosclerosis.

Illustrative examples of straight or branched saturated hydrocarbon chains having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

The term alkylthio having from 1 to 6 carbon atoms means the group $C_{1-6}$alkyl-S- wherein the alkyl moiety is straight or branched.

A 5- or 6-membered monocyclic or fused bicyclic heterocycle is a monocyclic or fused bicyclic aromatic ring containing at least 1 to 4 heteroatoms in at least one ring, such as nitrogen, oxygen, or sulfur or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, oxazolyl, isoxazolyl, triazolyl, tetrazolyl, thiazolyl, imidazolyl, benzothiazolyl, indolyl, quinolinyl, isoquinolinyl, or N-oxides of heterocycles containing a nitrogen atom.

More specifically, such a heterocycle may be a 2- or 3-thienyl; 2- or 3-furanyl; 2-, or 3-, or 4-pyridyl or 2-, 3-, or 4-pyridyl-N-oxide; 2-, 4-, or 5-pyrimidinyl; 3- or 4-pyridazinyl; 2-pyrazinyl; 2-pyrazinyl-N-oxide; 2- or 3-pyrrolyl; 3-, 4-, or 5-pyrazolyl; 2-, 4-, or 5-thiazolyl; 3-, 4-, or 5-isoxazolyl; 2-, 4-, or 5-oxazolyl; 3-, 4-, or 5-isothiazolyl; 5-tetrazolyl; 3- or 5-(1,2,4,-)triazolyl; 4- or 5-(1,2,3-)triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

Preferred compounds of this invention are those wherein one of $R_1$ and $R_2$ is substituted phenyl or more preferred are compounds wherein $R_1$ is hydrogen and $R_2$ is phenyl disubstituted in the 2,6-positions. More preferred are compounds wherein $R_1$ is hydrogen, $R_2$ is phenyl disubstituted in the 2,6-positions and $R_3$ is phenyl, substituted phenyl, or a straight or branched hydrocarbon chain having from 1 to 20 carbon atoms which is saturated or contains from 1 to 3 double bonds.

Pharmaceutically acceptable salts of the compounds of Formula I are also included as a part of the present invention.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, J Pharm Sci 16, 1–19 (1977).

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Certain compounds of the present invention may also exist in different stereoisomeric forms by virtue of the presence of asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers in chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, Biochemica et Biophysica 712:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed as $IC_{50}$ values; i.e., the concentration of test compound required to inhibit the activity of the enzyme by 50%.

TABLE 1

| Example | IAI $IC_{50}$ (μM) |
|---------|---------------------|
| 1 | 27.0 |
| 2 | 14.0 |
| 3 | 6.8 |
| 5 | >10 |
| 6 | 8.7 |
| 7 | 35 |
| 8 | 16 |
| 9 | 5.0 |

In one in vivo screen designated APCC, male Sprague-Dawley rats (200 to 225 g) were randomly divided into treatment groups and dosed at 4 PM with either vehicle (CMC/Tween) or suspensions of compounds in vehicle (30 mg/kg). The normal chow diet was then replaced with a high fat, high cholesterol diet with 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2.

TABLE 2

| Example | % Change (mg/dl) |
|---------|------------------|
| 1 | −56 |
| 2 | −42 |
| 3 | −75 |
| 5 | −31 |
| 6 | −43 |
| 7 | −51 |
| 8 | −68 |
| 9 | −58 |

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound an water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of general Formula I are prepared as generally set forth in Chart I hereof wherein $R_1$, $R_2$, and $R_3$ have the meanings defined in Formula I.

An amine of the formula $NHR_1R_2$ is reacted with chlorosulfonyl isocyanate in an appropriate organic solvent, such as $Et_2O$, THF, $CH_2Cl_2$, at 0° C. or less. The resulting chlorosulfonylurea may be isolated or used in situ. It is reacted with an alcohol of the formula $R_3OH$ in the presence of an acid scavenger such as triethylamine to give the desired oxysulfonylureas. These can be converted to their base addition salts by reacting with the appropriate metal or amine base. Compounds of Formula I wherein R is other than hydrogen are prepared by alkylating the base salt with a suitable alkylating agent of the formula R—I wherein R is as defined above and is other than hydrogen and I is iodine.

The amines $NHR_1R_2$, and alcohols, $R_3OH$, are known in the art or are prepared by procedures generally known in the art.

The following specific examples further illustrate the preparation of compounds of the invention.

EXAMPLE 1

Synthesis of Hexyl [[[2,6-bis(1-methylethyl)phenyl]amino]carbonyl]sulfamate

A solution of [[[2,6-bis(1-methylethyl)phenyl]amino]carbonyl]sulfamoyl chloride (5.0 g, 15.7 mmoles) in 80 mL THF was added dropwise to a solution of n-hexanol (1.60 g, 15.7 mmoles) and excess triethylamine (~3 mL) in 150 mL THF at room temperature under an atmosphere of $N_2$. This was stirred for 16 hours and then concentrated in vacuo. The residue was partitioned between 1N HCl and EtOAc and the organic layer was dried with $MgSO_4$, filtered, and evaporated to give an oily tan solid. Trituration with acetone/hexanes (9:1) gave 1.56 g of the title compound as a white solid, mp 148°–151° C.

EXAMPLE 2

Octadecyl [[[2,6-bis(1-methylethyl)phenyl]amino]carbonyl]sulfamate

When in the general procedure of Example 1, an appropriate amount of n-octadecanol was substituted for n-hexanol, the title compound was obtained, mp 95°–98° C.

EXAMPLE 3

Dodecyl [[[2,6-bis(1-methylethyl)phenyl]amino]carbonyl]sulfamate

When in the general procedure of Example 1, an appropriate amount of n-dodecanol was substituted for n-hexanol, the title compound was obtained, mp 112°–115° C.

EXAMPLE 4

Synthesis of [[[2,6-bis(1-methylethyl)phenyl]amino]carbonyl]sulfamoyl chloride

A solution of 2,6-diisopropylaniline (30.0 g, 0.169 moles) in 150 mL Et$_2$O was added dropwise to a solution of N-chlorosulfonyl isocyanate (14.73 mL, 0.169 moles) in 100 mL Et$_2$O at −15° C. (acetone/ice bath) under an atmosphere of N$_2$. The resulting off-white suspension was stirred at −15° C. for 1 hour and the solid was collected by vacuum filtration. The solid was washed with hexanes and air dried to give 53.79 g (99%) of the title compound as a white solid, mp 130°–134° C.

EXAMPLE 5

Decyl [[[2,6-bis(1-methylethyl)phenyl]amino]carbonyl]sulfamate

When in the general procedure of Example 1, an appropriate amount of n-decyl alcohol was substituted for n-hexanol, the title compound was obtained, mp 133°–135° C.

EXAMPLE 6

(±) 1-Methylheptyl [[[2,6-bis(1-methylethyl)phenyl]amino]carbonyl]sulfamate

When in the general procedure of Example 1, an appropriate amount of 2-octanol was substituted for n-hexanol, the title compound was obtained, mp 109°–113° C.

EXAMPLE 7

2,6-bis(1-methylethyl)phenyl [[[2,6-bis(1-methylethyl)phenyl]amino]carbonyl]sulfamate When in the general procedure of Example 1, an appropriate amount of 2,6-diisopropylphenol was substituted for n-hexanol, the title compound was obtained, mp 186°–189° C.

EXAMPLE 8

(±) 1-Methylundecyl [[[2,6-bis(1-methylethyl)phenyl]amino]carbonyl]sulfamate

When in the general procedure of Example 1, an appropriate amount of 2-dodecanol was substituted for n-hexanol, the title compound was obtained, mp 110°–112° C.

By following the general procedure of Example 1 only substituting the appropriate alcohol for n-hexanol the following compounds can be prepared:

1-methyltridecyl [[[2,6-bis(1-methylethyl)phenyl]amino]carbonyl]sulfamate, 2,6-dimethylphenyl [[[2,6-bis(1-methylethyl)phenyl]amino]carbonyl]sulfamate, 2,6-dimethoxyphenyl [[[2,6-bis(1methylethyl)phenyl]amino]carbonyl]sulfamate, 2,4,6-trimethoxyphenyl [[[2,6-bis(1-methylethyl)phenyl]amino]carbonyl]sulfamate, phenyl [[[2,6-bis(1-methylethyl)phenyl]amino]carbonyl]sulfamate, 2,4-difluorophenyl [[[2,6-bis(1-methylethyl)phenyl]amino]carbonyl]sulfamate, 2,6-difluorophenyl [[[2,6-bis(1-methylethyl)phenyl]amino]carbonyl]sulfamate, 2,6-bis(1,1-dimethylethyl)phenyl [[[2,6-bis(1-methylethyl)phenyl]amino]carbonyl]sulfamate, and 2,6-bis(1,1-dimethylethyl)-4-methylphenyl [[[2,6-bis(1-methylethyl)phenyl]amino]carbonyl]sulfamate, and 2,6-bis(1,1-dimethylethyl)-4-methoxyphenyl [[[2,6-bis(1-methylethyl)phenyl]amino]carbonyl]sulfamate.

EXAMPLE 9

Synthesis of Dodecyl [[[2,6-bis(1-methylethyl)phenyl]amino]carbonyl]sulfamate, sodium salt A solution of dodecyl [[[2,6-bis(1-methylethyl)phenyl]amino]carbonyl]sulfamate (2.85 g, 6.08 mmol) in 75 mL THF was added dropwise to a suspension of sodium hydride (0.24 g, 60% dispersion in mineral oil, 6.08 mmol) in 25 mL THF at 0° C. under an atmosphere of nitrogen. The resulting solution was stirred at 0° C. for 2 hours, concentrated in vacuo, and the residue was taken up in hot hexanes and filtered. The filtrate was concentrated to give 2.62 g of an off-white foam. $^1$H NMR (CDCl$_3$) δ7.09 (bs, 1H), 7.05–7.03 (m, 3H), 3.83 (m, 2H), 3.22 (m, 2H), 1.53 (m, 2H), 1.24 (bs, 18H), 1.10 (d, 12H), 0.85 (t, 3H).

EXAMPLE 10

Synthesis of Dodecyl [[[2,6-bis(1-methylethyl)phenyl]methylamino]carbonyl]sulfamate 1,8-Diazabicyclo[5.4.0]undec-7-ene is added to a solution of dodecyl [[[2,6-bis(1-methylethyl)phenyl]amino]carbonyl]sulfamate and methyl iodide in acetonitrile. The resulting solution is stirred at room temperature for 16 hours. The compound is isolated by diluting with ethyl acetate and washing with 1N HCl, followed by chromatography to give the title compound.

CHART I

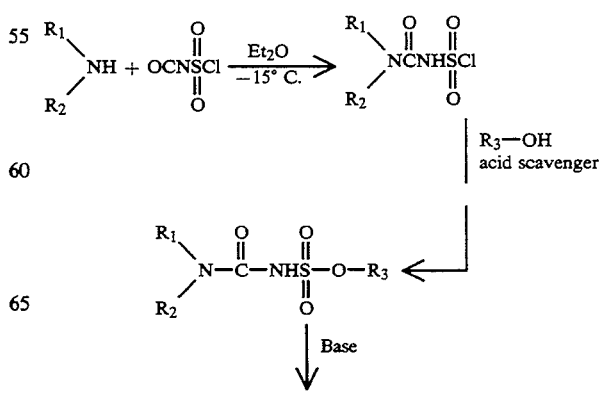

-continued
CHART I

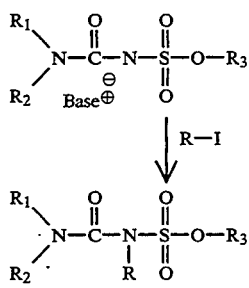

We claim:
1. A compound of the formula

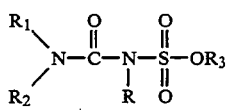
Formula I wherein R is hydrogen, a straight or branched alkyl group having from 1 to 8 carbon atoms or benzyl;
wherein each of $R_1$ and $R_2$ is selected from
(a) hydrogen,
(b) the group

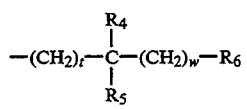

wherein t is zero to 4; w is zero to 4 with the proviso that the sum of t and w is not greater than 5; $R_4$ and $R_5$ are independently selected from hydrogen or alkyl having from 1 to 6 carbon atoms, or when $R_4$ is hydrogen, $R_5$ is selected from the group defined for $R_6$; and $R_6$ is phenyl or phenyl substituted with from 1 to 3 substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —$(CH2)_q NR_7 R_8$ wherein $R_7$ and $R_8$ are independently hydrogen or alkyl of from 1 to 4 carbon atoms, and q is zero or one;
(c) a straight or branched hydrocarbon chain having from 1 to 20 carbon atoms and which is saturated or contains from 1 to 3 double bonds;
(d) an alkyl group having from 1 to 6 carbon atoms wherein the terminal carbon is substituted with hydroxy, —$NR_7 R_8$ wherein $R_7$ and $R_8$ have the meanings defined above, or —COOalkyl wherein alkyl is straight or branched and has from 1 to 4 carbon atoms;
(e) —$(CH2)_p Q$ wherein p is a number from zero to 3 and Q is a 5- or 6-membered monocyclic or fused bicyclic heterocyclic ring having only one nitrogen, oxygen, or sulfur atom as the heteroatom in the heterocyclic ring;
(f) phenyl substituted with from 1 to 3 substituents selected from straight or branched alkyl having from 1 to 6 carbon atoms, alkoxy which is straight or branched and has from 1 to 6 carbon atoms, alkylthio which is straight or branched and has from 1 to 6 carbon atoms, —$(CH2)_q NR_7 R_8$ wherein q, $R_7$ and $R_8$ have the meanings defined above, hydroxy, nitro, chlorine, fluorine, bromine, or trifluoromethyl; or
(g) $NR_1 R_2$ taken together form a monocyclic heterocyclic group selected from pyrrolidino, piperidino, morpholino, or piperazino, each of which is unsubstituted or is substituted with one substituent selected from benzhydryl, straight or branched alkyl having from 1 to 6 carbon atoms, phenyl, benzyl, or substituted phenyl or substituted benzyl having 1 to 3 substituents selected from straight or branched alkyl having from 1 to 4 carbon atoms, straight or branched alkoxy having from 1 to 4 carbon atoms, hydroxy, fluorine, chlorine, bromine, trifluoromethyl, or nitro;
wherein $R_3$ is selected from
(a) phenyl which is unsubstituted or is substituted with from 1 to 3 substituents selected from:
phenyl,
an alkyl group having from 1 to 6 carbon atoms and which is straight or branched,
an alkoxy group having from 1 to 6 carbon atoms and which is straight or branched,
phenoxy,
hydroxy,
fluorine,
chlorine,
bromine,
nitro,
trifluoromethyl,
—COOH,
—COOalkyl wherein alkyl has from 1 to 4 carbon atoms and is straight or branched,
—$(CH2)_s NR_9 R_{10}$ wherein s is zero or one, and each of $R_9$ and $R_{10}$ is selected from hydrogen or a straight or branched alkyl group having 1 to 4 carbon atoms;
(b) 1- or 2-naphthyl which is unsubstituted or substituted with from 1 to 3 substituents selected from
phenyl,
an alkyl group having from 1 to 6 carbon atoms and which is straight or branched;
an alkoxy group having from 1 to 6 carbon atoms and which is straight or branched,
hydroxy,
phenoxy,
fluorine,
chlorine,
bromine,
nitro,
trifluoromethyl,
—COOH,
—COOalkyl wherein alkyl has from 1 to 4 carbon atoms and is straight or branched,
—$(CH2)_s NR_9 R_{10}$ wherein s, $R_9$ and $R_{10}$ have the meanings defined above;
(c) the group

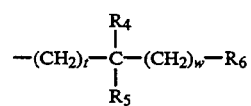

wherein t, w, $R_4$, $R_5$, and $R_6$ have the meanings defined hereinabove;
(d) —$(CH2)_p$—Q wherein p and Q have the meanings defined hereinabove;

or a pharmaceutically acceptable salt thereof with the provisos that:
(i) both $R_1$ and $R_2$ are not hydrogen at the same time;
(ii) when each of $R_1$ and $R_2$ is the group

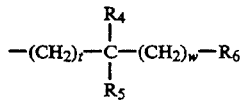

$R_5$ is hydrogen or alkyl having from 1 to 6 carbon atoms;
(iii) the following compounds are excluded:

2. A compound of claim 1 wherein one of $R_1$ and $R_2$ is substituted phenyl.

3. A compound of claim 2 wherein one of $R_1$ and $R_2$ is phenyl disubstituted in the 2,6-positions.

4. A compound of claim 1 wherein $R_1$ is hydrogen.

5. A compound of claim 4 wherein $R_3$ is phenyl or substituted phenyl.

6. A compound of claim 5 wherein $R_2$ is substituted phenyl.

7. A compound of claim 6 wherein $R_2$ is phenyl disubstituted on the 2,6-positions.

8. A compound of claim 7 wherein $R_3$ is phenyl disubstituted on the 2,6-positions.

9. A compound of claim 1 which is 2,6-bis(1-methylethyl)phenyl [[[2,6-bis(1-methylethyl)phenyl]amino]carbonyl]sulfamate.

| $R_1$ | $R_2$ | $R_3$ |
|---|---|---|
|  n-C$_4$H$_9$ |  H | 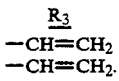 —CH=CH$_2$ |
| H | n-C$_4$H$_9$ | —CH=CH$_2$. |

10. A pharmaceutical composition comprising a compound of

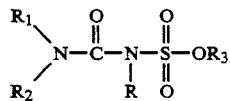

wherein R is hydrogen, a straight or branched alkyl group having from 1 to 8 carbon atoms, or benzyl;
wherein each of $R_1$ and $R_2$ is selected from
(a) hydrogen,
(b) the group

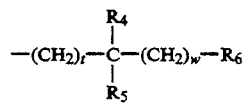

wherein t is zero to 4; w is zero to 4 with the proviso that the sum of t and w is not greater than 5; $R_4$ and $R_5$ are independently selected from hydrogen or alkyl having from 1 to 6 carbon atoms, or when $R_4$ is hydrogen, $R_5$ is selected from the group defined for $R_6$; and $R_6$ is phenyl or phenyl substituted with from 1 to 3 substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms, or —(CH$_2$)$_q$NR$_7$R$_8$ wherein $R_7$ and $R_8$ are independently hydrogen or alkyl of from 1 to 4 carbon atoms, and q is zero or one;

(c) a straight or branched hydrocarbon chain having from 1 to 20 carbon atoms and which is saturated or contains from 1 to 3 double bonds;

(d) an alkyl group having from 1 to 6 carbon atoms wherein the terminal carbon is substituted with hydroxy, —NR$_7$R$_8$ wherein $R_7$ and $R_8$ have the meanings defined above, or —COOalkyl wherein alkyl is straight or branched and has from 1 to 4 carbon atoms;

(e) —(CH$_2$)$_p$Q wherein p is a number from zero to 3 and Q is a 5 -or 6-membered monocyclic or fused bicyclic heterocyclic ring having only one nitrogen, oxygen, or sulfur atom as the heteroatom in the heterocyclic ring;

(f) phenyl substituted with from 1 to 3 substituents selected from straight or branched alkyl having from 1 to 6 carbon atoms, alkoxy which is straight or branched and has from 1 to 6 carbon atoms, alkylthio which is straight or branched and has from 1 to 6 carbon atoms, —(CH$_2$)$_q$NR$_7$R$_8$ wherein q, $R_7$ and $R_8$ have the meanings defined above, hydroxy, nitro, chlorine, fluorine, bromine, or trifluoromethyl; or (g) NR$_1$R$_2$ taken together form a monocyclic heterocyclic group selected from pyrrolidino, piperidino, morpholino, or piperazino, each of which is unsubstituted or is substituted with one substituent selected from benzhydryl, straight or branched alkyl having from 1 to 6 carbon atoms, phenyl, benzyl, or substituted phenyl or substituted benzyl having 1 to 3 substituents selected from straight or branched alkyl having from 1 to 4 carbon atoms, straight or branched alkoxy having from 1 to 4 carbon atoms, hydroxy, fluorine, chlorine, bromine, trifluoromethyl, or nitro;

wherein $R_3$ is selected from
(a) phenyl which is unsubstituted or is substituted with from 1 to 3 substituents selected from: phenyl,
an alkyl group having from 1 to 6 carbon atoms and which is straight or branched,
an alkoxy group having from 1 to 6 carbon atoms and which is straight or branched,
phenoxy,
hydroxy,
fluorine,
chlorine,
bromine,
nitro,
trifluoromethyl,
—COOH,
—COOalkyl wherein alkyl has from 1 to 4 carbon atoms and is straight or branched,
—(CH$_2$)$_s$NR$_9$R10 wherein s is zero or one, and each of $R_9$ and R$_{10}$ is selected from hydrogen or a straight or branched alkyl group having 1 to 4 carbon atoms;

(b) 1- or 2-naphthyl which is unsubstituted or substituted with from 1 to 3 substituents selected from phenyl,
an alkyl group having from 1 to 6 carbon atoms and which is straight or branched;
an alkoxy group having from 1 to 6 carbon atoms and which is straight or branched,
hydroxy,
phenoxy,
fluorine, chlorine,
bromine,
nitro,
trifluoromethyl,
—COOH,
—COOalkyl wherein alkyl has from 1 to 4 carbon atoms and is straight or branched,
—$(CH_2)_s NR_9 R_{10}$ wherein s, $R_9$ and $R_{10}$ have the meanings defined above;

(c) the group

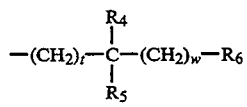

wherein t, w, $R_4$, $R_5$, and $R_6$ have the meanings defined hereinabove;

(d) —$(CH_2)_p$—Q wherein p and Q have the meanings defined hereinabove;

or a pharmaceutically acceptable salt thereof with the provisos that (i) both $R_1$ and $R_2$ are not hydrogen at the same time;

(ii) when each of $R_1$ and $R_2$ is the group

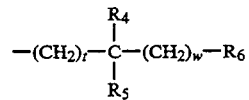

$R_5$ is hydrogen or alkyl having from 1 to 6 carbon atoms; and (iii) the following compounds are excluded:

| $R_1$ | $R_2$ | $R_3$ |
|---|---|---|
| n-$C_4H_9$ | H | —CH=$CH_2$ |
| H | n-$C_4H_9$ | —CH=$CH_2$. |

11. A method of treating hypercholesterolemia and lowering blood cholesterol in a patient in need thereof which comprises administering to said patient an effective amount of a composition of claim 10.

* * * * *

UNITED STATES PATENT AND TRADEMARK OFFICE
CERTIFICATE OF CORRECTION

PATENT NO. : 5,364,882
DATED : Nov. 15, 1994
INVENTOR(S) : Picard et al.

It is certified that error appears in the above-identified patent and that said Letters Patent is hereby corrected as shown below:

Column 12, line 34, "$-(CH2)_sNR9R10$" should read "$-(CH_2)_sNR_9R_{10}$".

Column 13, line 15 after "excluded:" insert

| $R_1$ | $R_2$ | $R_3$ |
|---|---|---|
| n-$C_4H_9$ | H | -CH=$CH_2$ |
| H | n-$C_4H_9$ | -CH=$CH_2$ |

Column 13, line 33 delete

" 
| $R_1$ | $R_2$ | $R_3$ |
|---|---|---|
| n-$C_4H_9$ | H | -CH=$CH_2$ |
| H | n-$C_4H_9$ | -CH=$CH_2$ |
"

Signed and Sealed this

Sixth Day of June, 2000

Attest:

Q. TODD DICKINSON

*Attesting Officer*     *Director of Patents and Trademarks*